(12) United States Patent
Muraki et al.

(10) Patent No.: US 9,036,017 B2
(45) Date of Patent: May 19, 2015

(54) BIOLOGICAL OBSERVATION APPARATUS AND BIOLOGICAL OBSERVATION METHOD

(75) Inventors: Kayuri Muraki, Kuki (JP); Hiroshi Wakai, Hamura (JP)

(73) Assignee: OLYMPUS CORPORATION, Tokyo (JP)

( * ) Notice: Subject to any disclaimer, the term of this patent is extended or adjusted under 35 U.S.C. 154(b) by 1280 days.

(21) Appl. No.: 12/884,319

(22) Filed: Sep. 17, 2010

(65) Prior Publication Data

US 2011/0009744 A1    Jan. 13, 2011

Related U.S. Application Data

(63) Continuation of application No. PCT/JP2009/055327, filed on Mar. 18, 2009.

(30) Foreign Application Priority Data

Mar. 21, 2008   (JP) ................... 2008-074361

(51) Int. Cl.
*H04N 9/47*   (2006.01)
*G02B 21/00*  (2006.01)
*G01N 21/64*  (2006.01)
(Continued)

(52) U.S. Cl.
CPC ........ *G02B 21/0004* (2013.01); *G01N 21/6456* (2013.01); *G02B 21/16* (2013.01); *G02B 21/365* (2013.01)

(58) Field of Classification Search
CPC ........... G01N 21/6456; G02B 21/0004; G02B 21/16; G02B 21/365; A61B 1/041; A61B 1/00036; A61B 1/0005; A61B 19/52; H04N 7/18

USPC ........................................... 348/77
See application file for complete search history.

(56) References Cited

U.S. PATENT DOCUMENTS 6,293,911 B1 *  9/2001  Imaizumi et al. ............. 600/160
7,009,700 B2 *  3/2006  Dubois et al. ................. 356/317
7,164,471 B2 *  1/2007  Yonetani et al. .............. 356/124
(Continued)

FOREIGN PATENT DOCUMENTS

JP    10-201707    8/1998
JP    2003-93339   4/2003
(Continued)

OTHER PUBLICATIONS

"Official Journal of the Society for Molecular Imaging", vol. 5, No. 3, Jul. 2006, abstracts, p. 240.
(Continued)

*Primary Examiner* — Andy Rao
*Assistant Examiner* — Shan Elahi
(74) *Attorney, Agent, or Firm* — Scully, Scott, Murphy & Presser, P.C.

(57) ABSTRACT

A biological observation apparatus is configured as follows. Namely, the biological observation apparatus includes a marker attached to a living body in order to detect the vibration of the living body, a high-sensitivity camera which forms an observation image of the living body, a high-speed camera which forms an image of light from the marker, and an optical system including a first BA which prevents the light from the marker from entering the high-sensitivity camera.

8 Claims, 2 Drawing Sheets

(51) Int. Cl.
　　*G02B 21/16*　　　(2006.01)
　　*G02B 21/36*　　　(2006.01)

(56) References Cited

U.S. PATENT DOCUMENTS

| | | | |
|---|---|---|---|
| 7,289,199 B2* | 10/2007 | Yonetani et al. | 356/124 |
| 7,592,139 B2* | 9/2009 | West et al. | 435/6.11 |
| 7,593,040 B2* | 9/2009 | Shan et al. | 348/208.99 |
| 8,426,135 B1* | 4/2013 | West et al. | 435/6.12 |
| 2002/0028503 A1* | 3/2002 | Ackley et al. | 435/287.2 |
| 2002/0036264 A1* | 3/2002 | Nakasuji et al. | 250/306 |
| 2002/0095073 A1* | 7/2002 | Jacobs et al. | 600/300 |
| 2003/0048933 A1* | 3/2003 | Brown et al. | 382/128 |
| 2003/0146100 A1* | 8/2003 | Huang et al. | 204/547 |
| 2003/0151735 A1* | 8/2003 | Blumenfeld et al. | 356/73 |
| 2004/0063216 A1* | 4/2004 | Lubocki | 436/173 |
| 2004/0106189 A1* | 6/2004 | Dodgson et al. | 435/285.2 |
| 2004/0114219 A1* | 6/2004 | Richardson | 359/368 |
| 2004/0126279 A1* | 7/2004 | Renzi et al. | 422/100 |
| 2004/0265889 A1* | 12/2004 | Durham et al. | 435/6 |
| 2005/0095602 A1* | 5/2005 | West et al. | 435/6 |
| 2005/0179892 A1* | 8/2005 | Gerstner et al. | 356/318 |
| 2005/0237423 A1* | 10/2005 | Nilson et al. | 348/370 |
| 2006/0050376 A1* | 3/2006 | Houston et al. | 359/392 |
| 2007/0159687 A1* | 7/2007 | Tohma et al. | 359/368 |
| 2008/0265130 A1* | 10/2008 | Colomb et al. | 250/201.9 |
| 2009/0068062 A1* | 3/2009 | Jafari et al. | 422/64 |
| 2009/0086314 A1* | 4/2009 | Namba et al. | 359/383 |
| 2009/0215023 A1* | 8/2009 | West et al. | 435/4 |
| 2010/0321493 A1* | 12/2010 | Huber et al. | 348/143 |

FOREIGN PATENT DOCUMENTS

| | | |
|---|---|---|
| JP | 2006-112993 | 4/2006 |
| JP | 2007-171005 | 7/2007 |
| JP | 2007-187810 | 7/2007 |

OTHER PUBLICATIONS

International Search Report dated Jun. 2, 2009.
English translation of International Preliminary Report on Patentability together with the Written Opinion dated Nov. 11, 2010.

* cited by examiner

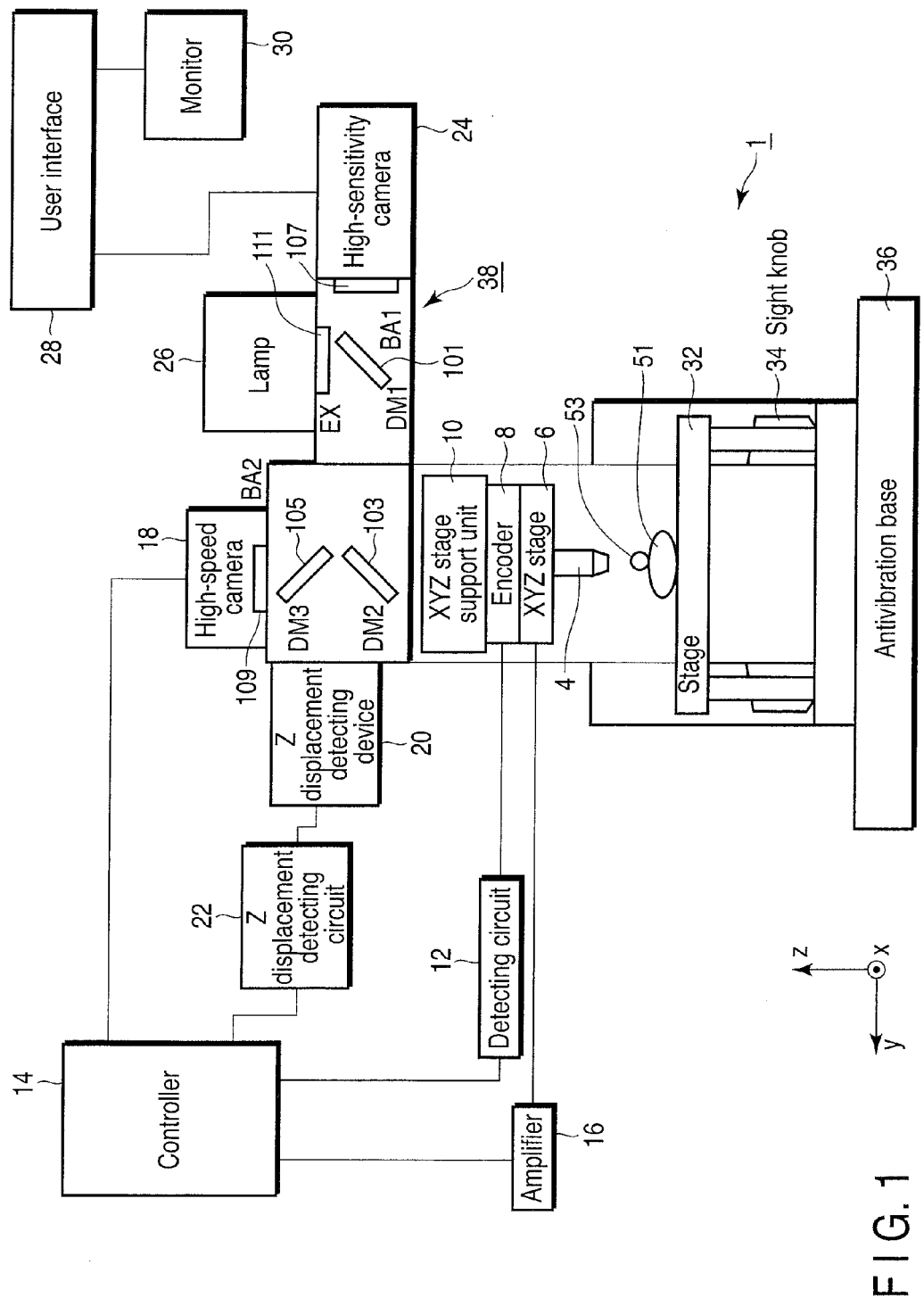
F I G. 1

US 9,036,017 B2

BIOLOGICAL OBSERVATION APPARATUS AND BIOLOGICAL OBSERVATION METHOD

CROSS-REFERENCE TO RELATED APPLICATIONS

This is a Continuation Application of PCT Application No. PCT/JP2009/055327, filed Mar. 18, 2009, which was published under PCT Article 21(2) in Japanese.

This application is based upon and claims the benefit of priority from prior Japanese Patent Application No. 2008-074361, filed Mar. 21, 2008, the entire contents of which are incorporated herein by reference.

BACKGROUND OF THE INVENTION

1. Field of the Invention

The present invention relates to a biological observation apparatus and biological observation method.

2. Description of the Related Art

Generally, when precisely observing a living body by using a biological observation apparatus, a biological vibration as the vibration of the living body to be observed poses a serious problem.

In biological observation, a living body to be observed is observed as it is dyed with any of various dyes such as a fluorescent dye or light-emitting dye. Since light from any of these dyes is very weak, an image of the living body is normally sensed by using a high-sensitivity camera.

For example, the technique disclosed in Jpn. Pat. Appln. KOKAI Publication No. 2007-187810 detects the vibration of a living body as an observation target by using a vibration detecting camera having a frame rate (to be referred to as an FPS hereinafter) higher than that of a high-sensitivity camera.

Since light from a living body is weak as described above, however, the exposure time must be set to a certain long time in order to sense an image of the feature point of the living body. That is, it is necessary to decrease the FPS. This decrease in FPS makes high-accuracy control impossible. In other words, if the FPS is set at a value capable of achieving high-accuracy control, it becomes difficult to detect a biological vibration by using the feature point of the living body.

Under the circumstances, the following technique is proposed in, e.g., "Official Journal of the Society for Molecular Imaging", vol. 5, July, 2006, abstracts, p. 240. That is, according to "Official Journal of the Society for Molecular Imaging", vol. 5, July, 2006, abstracts, p. 240, a marker for detecting a biological vibration is attached to a living body to be observed. This makes high-accuracy biological observation and biological vibration control possible.

In the technique disclosed in non-patent reference 1 described above, however, the above-mentioned marker is taken in an observation image, as shown in FIG. 3. If an exposure time suitable for the observation of a living body is set for an observation image like this, so-called smear-blooming occurs due to a high contrast between the marker and living body.

That is, in the technique disclosed in "Official Journal of the Society for Molecular Imaging", vol. 5, July, 2006, abstracts, p. 240, the exposure time of a high-sensitivity camera for sensing an observation image must be shortened, and this prevents precise observation.

BRIEF SUMMARY OF THE INVENTION

The present invention has been made in consideration of the above situation, and has as its object to provide a biological observation apparatus and biological observation method using a marker for accurately detecting a biological vibration, and capable of precise biological observation by preventing the marker from being taken in an observation image.

According to a first aspect of the present invention, there is provided a biological observation apparatus for observing a living body, comprising:

a marker unit attached to the living body to detect a vibration of the living body;

an observation image sensing unit which forms an observation image of the living body;

a vibration detecting image sensing unit which detects light from the marker unit; and an optical system comprising a filtering unit which prevents the light from the marker unit from entering the observation image sensing unit.

According to a second aspect of the present invention, there is provided a biological observation apparatus for observing a living body, comprising:

a marker unit attached to the living body to detect a vibration of the living body;

an observation image sensing unit which forms an observation image of the living body; and a vibration detecting image sensing unit which detects light from the marker unit, wherein an image sensing visual field of the observation image sensing unit and a detection region of the vibration detecting image sensing unit are different regions.

According to a third aspect of the present invention, there is provided a biological observation apparatus for observing a living body, comprising:

a marker unit attached to the living body to detect a vibration of the living body;

an observation image sensing unit which forms an observation image of the living body;

a vibration detecting image sensing unit which detects light from the marker unit; and an optical system comprising a spectral unit which prevents the light from the marker unit from entering the observation image sensing unit.

According to a fourth aspect of the present invention, there is provided a biological observation method for observing a living body, comprising:

Attaching a marker to the living body to detect a vibration of the living body;

Sensing an observation image of the living body;

Performing a filtering process for preventing an image of light from the marker from being sensed in the sensing; and Detecting the light from the marker.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing a configuration example of a biological observation apparatus according to an embodiment of the present invention;

DETAILED DESCRIPTION OF THE INVENTION

Figure 2:
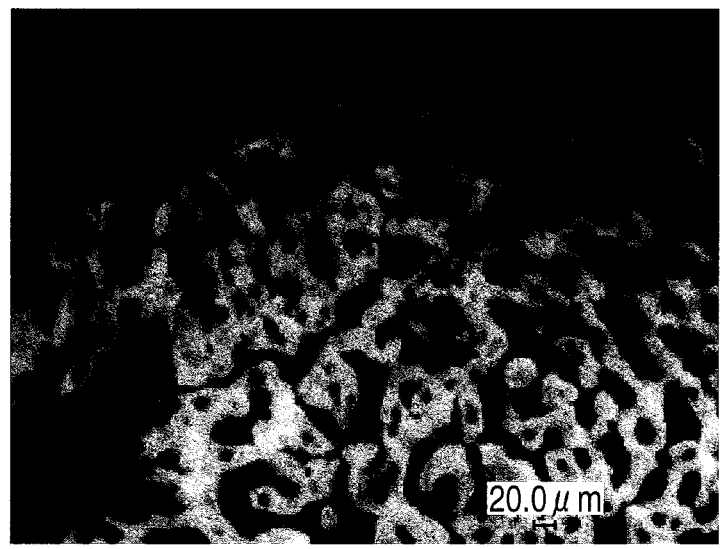
FIG. 2 is a view showing an image of an observation target living body sensed by a high-sensitivity camera of the biological observation apparatus according to the embodiment of the present invention.
Figure 3:
FIG. 3 is a view showing an image of an observation target living body sensed by a conventional biological observation apparatus.

An embodiment of the present invention will be explained below with reference to the accompanying drawings. Although the embodiment will be explained by taking the form of a microscope as an example, the present invention is also applicable to another biological observation apparatus such as an endoscope.

FIG. 1 is a view showing a configuration example of the biological observation apparatus according to the embodiment of the present invention. As shown in FIG. 1, a biological observation apparatus 1 includes an objective lens 4, XYZ stage 6, encoder 8, XYZ stage support unit 10, detecting circuit 12, controller 14, amplifier 16, high-speed camera 18, Z-displacement detecting device 20, Z-displacement detecting circuit 22, high-sensitivity camera 24, lamp 26, user interface 28, monitor 30, stage 32, sight knob 34, antivibration base 36, and optical system 38.

The optical system 38 is one principal feature unit of the biological observation apparatus according to this embodiment, and includes a first DM (Dichroic Mirror) 101, second DM 103, third DM 105, first BA (Barrier Filter) 107, second BA (Barrier Filter) 109, and EX (Excitation Filter) 111.

Note that an observation target living body 51 to which a marker 53 is attached is placed on the stage 32.

The objective lens 4 is attached to the XYZ stage 6 connected to the encoder 8, and is supported by the XYZ stage support unit 10.

The XYZ stage 6 supports the objective lens 4 such that it can move in the X, Y, and Z directions.

The encoder 8 detects the displacement of the XYZ stage 6, and outputs the detection result to the detecting circuit 12.

The detecting circuit 12 detects the position of the XYZ stage 6 based on the output from the encoder 8.

The controller 14 comprehensively controls each unit of the biological observation apparatus 1. For example, the controller 14 performs a position control operation of the XYZ stage 6, based on the position of the XYZ stage 6 detected by the detecting circuit 12 and information from the high-speed camera (to be described later).

The amplifier 16 amplifies a control signal output from the controller 14, and supplies the amplified signal to the XYZ stage 6, thereby moving the position of the XYZ stage 6.

Although details will be described later, the high-speed camera 18 is a camera that is adjusted to focus on the marker 53, and senses an image of the marker 53. Note that the high-speed camera 18 has an FPS higher than that of the high-sensitivity camera 24. By facilitating accurate detection of the above-mentioned marker by using this arrangement, it is possible to prevent a marker detection error and accurately suppress an image blur.

The Z-displacement detecting device 20 is a device for detecting the displacement of the observation target living body 51 in the Z direction. The Z-displacement detecting device 20 is, e.g., a device for transmitting and receiving a laser beam. The Z-displacement detecting device 20 receives light reflected by the observation target living body 51 illuminated with this laser beam, and outputs the result of the transmission/reception of the laser beam to the Z-displacement detecting circuit 22.

That is, the Z-displacement detecting device 20 has the arrangement of, e.g., a laser displacement meter. Note that if the output changes in accordance with, e.g., the type of the objective lens 4, correction is naturally performed by a predetermined correction expression.

Based on the output from the Z-displacement detecting device 20, the Z-displacement detecting circuit 22 detects the position of the observation target living body 51 in the Z direction, and outputs the detection result to the controller 14. The controller 14 performs the position control operation of the XYZ stage 6 based on the position of the observation target living body 51 detected by the Z-displacement detecting circuit 22. The amplifier 16 amplifies a control signal output from the controller 14, and supplies the amplified signal to the XYZ stage 6, thereby moving the position of the XYZ stage 6.

Although details will be described later, the high-sensitivity camera 24 is a camera that focuses on only the observation target living body 51, and performs image sensing for acquiring a precise observation image of the observation target living body 51.

The lamp 26 is a light source for performing illumination necessary for observation and detection through the EX 111.

The user interface 28 is an interface for allowing a user to set various conditions such as the observation conditions.

The monitor 30 is a display means for displaying, e.g., an observation image acquired by image sensing performed by, e.g., the high-speed camera 18 or high-sensitivity camera 24.

The stage 32 is a stage for placing the observation target living body 51 thereon.

The sight knob 34 is a member for adjusting the position of the objective lens 4 in the Z direction.

Note that the X, Y, and Z directions are respectively indicated by the X-, Y-, and Z-axes in FIG. 1.

The antivibration base 36 is an antivibration member for suppressing external vibrations applied to the biological observation apparatus 1.

The optical system 38 as one principal feature of the biological observation apparatus 1 according to this embodiment will be explained in detail below.

(Light Emitted by Lamp 26)

Light emitted by the lamp 26 enters the first DM 101 through the EX 111, and is reflected toward the second DM 103 by the first DM 101. After that, the light is reflected toward the objective lens 4 by the second DM 103, and illuminates the observation target living body 51 through the objective lens 4.

(Fluorescence/Reflected Light from Observation Target Living Body 51)

The fluorescence/reflected light from the observation target living body 51 enters the second DM 103 through the objective lens 4, and is reflected toward the first BA 107 by the second DM 103. After being transmitted through the first DM 101, the fluorescence/reflected light enters the high-sensitivity camera 24 through the first BA 107.

Note that the first BA 107 is a barrier filter that removes light other than the light pertaining to biological information (the fluorescence/reflected light from the observation target living body 51). Therefore, only the light from the observation target living body 51 enters the high-sensitivity camera 24.

Light from the marker 53 is almost removed by the second DM 103, and further reduced by the first DM 101 and first BA 107. Accordingly, the high-sensitivity camera 24 does not sense the light from the marker 53. The high-sensitivity camera 24 forms only an observation image of the observation target living body 51.

(Fluorescence from Marker 53)

Fluorescence from the marker 53 is transmitted through the objective lens 4 and second DM 103, and enters the high-speed camera 18 through the second BA 109. Note that the second BA 109 is a barrier filter that removes light other than the light from the marker 53.

That is, light other than the light from the marker 53 is removed by the second BA 109 after being transmitted through the second DM 103 and third DM 105.

Therefore, the high-speed camera 18 receives only the light from the marker 53 and forms an image of the light.

Note that the light from the marker 53 is reflected by the third DM 103, and enters the Z-displacement detecting device 20 as well.

The main differences between the high-speed camera 18 and high-sensitivity camera 24 will be explained below.

(FPS)

The FPS of the high-speed camera 18 is higher than that of the high-sensitivity camera 24.

(Exposure Time)

The exposure time of the high-speed camera 18 is shorter than that of the high-sensitivity camera 24.

(Targets of Image Sensing)

The high-speed camera 18 precisely senses an image of only the marker 53, and the high-sensitivity camera 24 precisely senses an image of only the observation target living body 51. That is, the high-speed camera 18 does not sense an image of the observation target living body 51, and precisely senses only an image of the marker 53. This facilitates image processing, and increases the accuracy. On the other hand, the high-sensitivity camera 24 senses only an image of the observation target living body 51. This makes precise biological observation feasible.

(Resolution)

The accuracy of biological observation can further be increased by making the resolution of the high-speed camera 18 higher than that of the high-sensitivity camera 24.

(Targets of Focusing)

The high-sensitivity camera 24 focuses on the observation target living body 51, and the high-speed camera 18 focuses on the marker 53. This makes it possible to precisely observe the observation target living body 51 and increase the accuracy of the detection of the marker 53 at the same time. That is, it is possible to accurately suppress an image blur and acquire a precise observation image.

The marker 53 will be explained in detail below.

(When Using Fluorescence Type Marker as Marker 53)

The marker 53 is formed such that fluorescence emitted by the marker 53 can be optically separated from fluorescence emitted by a dye (to be referred to as a living body dye hereinafter) having dyed the observation target living body 51. Note that excitation light for the fluorescence emitted by the marker 53 and excitation light for the living body dye may be the same or different, provided that it is possible to optically separate the fluorescence emitted by the marker 53 from the fluorescence emitted by the living body dye.

Also, the fluorescence intensity emitted by the marker 53 is more preferably at least, e.g., ten times that of the living body dye.

Furthermore, it is favorable to form the marker 53 and living body dye so that they correspond to excitation light in a broader wavelength region, and the wavelength regions of the fluorescence emitted by them are broad.

Note that when dyeing the observation target living body 51 by using, e.g., GFP (Green Fluoro Protein; which is excited by 488-nm excitation light), the marker 53 is preferably made of a material having a red fluorescence wavelength.

In addition, since the fluorescent material is much brighter than the living body dye, an image of the material can be sensed even by a high-speed camera.

(When Using Reflected Light Type Marker as Marker 53)

The marker 53 is given a surface that causes almost regular reflection in the direction of illumination light entering the marker 53. The excitation light for the living body dye can be used as the illumination light. Furthermore, white light can be used as the illumination light so as to reflect a larger amount of light (to increase the reflection efficiency).

Note that the reflection efficiency is much higher than the excitation efficiency of fluorescence, and the third DM 105 has a filtering effect. Therefore, the second BA 109 need not be formed when using the reflected light type marker.

In addition, when using reflected light by using the reflected light type marker as the marker 53, the wavelength region can be made broader than that when using fluorescence. Accordingly, a brighter marker image can be obtained. That is, since the FPS of the high-speed camera 18 can be set lower, it is possible to perform visual servo at a higher speed, and further increase the tracking accuracy.

The XYZ stage 6 will be explained in detail below.

The XYZ stage 6 includes an X-axis stage, Y-axis stage, and Z-axis stage. The X-axis stage can move forward and backward parallel to the scanning direction of the high-speed camera 18. The Y-axis stage can move forward and backward in a direction perpendicular to the X-axis stage. The Z-axis stage can move forward and backward in a direction parallel to the optical axis.

The encoder 8 is attached to the XYZ stage 6 as a position sensor for sensing the position of the XYZ stage 6. The stroke of the XYZ stage 6 is preferably twice or more the width of the vibration of the observation target living body 51.

The adjustment of the direction of the XYZ stage 6 will be explained in detail below.

First, the X-, Y-, and Z-axis stages are assembled perpendicularly to each other.

(Adjustment of Direction of XYZ Stage)

Although not shown, a transparent flat plate having linear plating on a portion of the upper surface is used. The plating formed on this flat plate is preferably longer than the visual field of the high-speed camera 18. The flat plate is held by an attaching jig (not shown). The attaching jig is fixed on the XYZ stage 6 to which the objective lens 4 having a low magnification (wide visual field) is attached. In this state, the end portion of the plating on the flat plate is positioned parallel to the moving direction of the X-axis stage, and in the center of the visual field of the high-speed camera 18. When illuminating the flat plate with, e.g., white light, the light is reflected by the plating on the flat plate.

Note that the attaching jig may have a focusing adjusting mechanism for adjusting the focusing position. In this case, the focusing adjusting mechanism performs adjustment such that the upper surface of the flat plate is positioned in the focusing position of the objective lens 4. The attaching jig can further have an XY-direction adjusting function. In this arrangement, the XY-direction adjusting function performs adjustment such that the end portion of the plating is positioned in the visual field to be projected on the high-speed camera 18.

In the arrangement described above, an adjusting mechanism (not shown) adjusts the direction of the XYZ stage 6 so that the straight line of the end portion of the plating is parallel to the visual field of the high-speed camera 18.

(Adjustment of Origin Position of XYZ Stage 6)

To increase the efficiency of the control operation performed by the controller 14, the origin position of the XYZ stage 6 is preferably matched with the center of the visual field of the high-speed camera 18. Note that cross plating is formed by thin lines on the above-mentioned flat plate, and the center of the cross formed on the flat plate is positioned in the origin position of the XYZ stage 6 when the flat plate is attached to the XYZ stage 6 as described above. Note also that the above-mentioned cross is formed to make an angle of 45° with the running direction of the XY stage.

An adjusting mechanism (not shown) shifts the position (in the direction perpendicular to the optical axis; the position in the Z direction) of the high-speed camera 18 such that the crossed lines intersect the four corners of the visual field of the high-speed camera 18. Note that this adjusting mechanism can be formed by, e.g., a plurality of screws and a leaf spring. In this mechanism, the force pushing the leaf spring can be adjusted by the screws.

The above explanation is based on the assumption that the visual field of the high-speed camera 18 is a square. When the visual field of the high-speed camera 18 is a rectangle, however, it is possible to use, e.g., the following arrangement.

That is, when the visual field of the high-speed camera 18 is a rectangle, the angle of the cross need only be adjusted so that the crossed lines intersect the four corners of the high-speed camera 18. In this case, it is possible to shift the position of the high-speed camera 18, or shift the origin position of the XYZ stage 6. Note that the origin position of the XYZ stage 6 can be shifted physically or by software.

This arrangement is simple because it is unnecessary to form the adjusting mechanism as described above. Also, a residual $\Delta x \Delta y$ of the vibration detected by image processing can directly be used as an error signal of the XY stage.

(Holding of XYZ Stage 6)

In the example shown in FIG. 1, the XYZ stage 6 is held together with the optical system 38. This arrangement facilitates matching the optical axis of the optical system 38 with that of the objective lens 4, and makes it possible to obtain a precise observation image.

It is, however, also possible to hold the XYZ stage 6 on a support table different from the support table of the optical system 38. In this case, the two support tables are arranged to match the optical axes of the objective lens 4 and optical system 38. This arrangement can increase the support rigidity, and can perform high-speed, high-accuracy tracking.

Note that the other support table described above is placed on the antivibration base 36, together with the biological observation apparatus. When both the other support table and biological observation apparatus are placed on the antivibration base 36, one reference position is determined, and this facilitates maintaining the optical performance by holding the positional relationship between them.

The other support table can also be placed on a base different from that of the optical system 38. When the operation of the XYZ stage 6 generates a vibration, this arrangement can prevent the vibration from being transmitted to the optical system 38.

Note that the form of support of the XYZ stage 6 can be the so-called cantilevered support, and can also be the so-called double end support. To track a target such as a living body that abruptly changes, however, the XYZ stage 6 is preferably supported by double end support having higher rigidity. On the other hand, when shortening the distance between the image forming optical system and objective lens 4 in order to maintain the optical performance, the XYZ stage 6 is preferably supported by cantilevered support.

The image processing performed by the controller 14 will be explained below.

First, the displacement amount of the observation target living body 51 in the X and Y directions is detected by the image processing. Subsequently, the image acquired by image sensing is binarized by a threshold value by using the center of the visual field of the high-speed camera 18 as the origin. In addition, the barycentric position of a bright region in the binarized image is obtained. This barycentric position is used as a present position in the control system.

The above processing matches the center of the visual field of the high-speed camera 18 with the origin of the XY stage. Accordingly, a value obtained by multiplying the result of the image processing by the resolution can directly be used in control.

Note that when the resolution changes in accordance with the magnification of the objective lens 4, the output operation must be changed in accordance with the objective lens 4. Therefore, it is favorable to, e.g., allow the user to select the type of the objective lens 4 presently being used in a pull-down menu or the like.

The control system of the controller 14 of the biological observation apparatus 1 will be explained below.

The controller 14 performs control based on the displacement amount in the X and Y directions detected as described above and an output value (command value) from the Z-displacement detecting circuit 22.

That is, the controller 14 performs a control operation by calculating, as an error signal, the difference between the displacement amount (command value) as described above and the position information of the XYZ stage 6 detected by the encoder 8 (detecting circuit 12) as a position sensor. The controller 14 performs D/A processing on the result of this control operation, performs an amplification process by the amplifier 16, and outputs the result to the XYZ stage 6.

Note that the weight and shape of the objective lens 4 change from one objective lens to another, so the control accuracy can be increased by changing the tuning of the controller 14 for each objective lens 4 to be actually used.

When using a so-called internal model or the like, an internal model to be used is preferably changed in accordance with the objective lens 4 to be actually used, because the internal model of the objective lens 4 changes from one objective lens to another. For example, it is possible to allow the user to select the type of the objective lens 4 to be used in a pull-down menu. It is also possible to automatically identify the type of the objective lens 4 by using an identification number such as a barcode indicating the model number near a screw portion of the objective lens 4.

The stage 32 will be explained below.

The stage 32 is a so-called sample table on which a small animal such as a mouse is placed. The stage 32 can move in the X and Y directions. Note that this movement of the stage 32 is preferably electrically driven.

When the stage 32 is moved by electrical drive, the position of the vibration of an organ of the observation target living body 51 can be moved by automatic control to a position where the optical performance and tracking performance are highest.

More specifically, the position of the observation target living body 51 (marker 53) that is not breathing can be moved by automatically controlling the stage 32 to a position almost matching the optical axis of the objective lens 4.

Also, when the stage 32 is moved by electrical drive, it is possible to form a state in which the optical performance is highest in a time zone during which observation is most stably possible. More specifically, the center of the amplitude of the total vibration including the respiration of the observation target living body 51 can be moved by automatically controlling the stage 32 to a position almost matching the optical axis of the objective lens 4.

Furthermore, when the stage 32 is moved by electrical drive, an average optical performance can be obtained at any timing.

In the biological observation apparatus 1 according to this embodiment as described above, the entire region of the vibration of the observation target living body 51 is held in a region close to the optical axis of the objective lens 4 to some extent. This suppresses the influence of light amount variations, and makes it possible to always stably detect the marker 53.

Accordingly, high-accuracy control can be achieved even when detecting the position of the stage 32 by using a position sensor having low detection performance in the two end portions of the stage 32.

Also, since the central portion of the stage 32 can stably be used, a large vibration of the observation target living body 51 can be tracked regardless of the direction of the vibration.

The procedure of biological observation performed by the biological observation apparatus according to this embodiment will be explained below.

First, the user activates the biological observation apparatus 1. More specifically, the user performs initialization by moving the stage 32 and XYZ stage 6 forward and backward along their entire strokes, and returning them to their origins (matching the optical axes).

Then, the user designates the objective lens 4 to be used in this biological observation, by operating the user interface 28. Based on this designation, the controller 14 optimizes, e.g., the resolution and the tuning of the control algorithm, i.e., optimizes the internal model.

Subsequently, the user designates an observation wavelength to be used in this biological observation, and optimizes the first DM 101, second DM 103, third DM 105, EX 111, first BA 107, and second BA 109, by operating the user interface 28.

The user cuts open the abdomen of the observation target living body 51 such as a small animal, and places the observation target living body 51 on the stage 32 immediately below the objective lens 4. In addition, the user places the marker 53 on an observation target organ of the observation target living body 51. More specifically, the user disperses the bead-like marker 53 in a physiological saline solution, and places the dispersion on the observation target organ.

After that, the user adjusts the position of the stage 32 such that the observation target organ is positioned below the objective lens 4. In addition, the user presses a preview button (not shown) of the user interface 28. When this preview button (not shown) is pressed, the monitor 30 displays an image of the high-sensitivity camera 24.

Note that it is, of course, also possible to set an ROI indicating a region where the marker 53 is to be placed, and display the ROI by superposing it on the image sensed by the high-sensitivity camera 24.

Subsequently, the user lowers the position of the objective lens 4 in the Z direction by rotating the sight knob 34. More specifically, the user lowers the objective lens 4 in the Z direction to a position where the observation target organ can stably be observed for as long a time period as possible. Note that the Z-direction adjusting function may be given to the stage 32 (instead of the XYZ stage 6).

Consequently, even when using a short-stroke stage such as a piezo stage as the XYZ stage 6, vibration suppression can be performed by maximally utilizing the stroke of the stage. Also, when the application voltage is 0 V for a piezo element at the origin as in the piezo stage, a time during which tracking can be performed with a low application voltage prolongs. This makes power saving possible.

Note that instead of lowering the objective lens 4 to the position where the observation target organ can stably be observed for as long a time period as possible as described above, the objective lens 4 may be lowered midway along the amplitude of the vibration of the observation target living body 51 in the Z direction.

This obviates the need to use the end portions of the stroke of the XYZ stage 6 operable in arbitrary directions, and stabilizes, e.g., the resolution of the XYZ stage 6. Also, the vibration of the observation target living body 51 occurs within a range having a margin in the vertical direction (Z direction), with respect to the origin of the XYZ stage 6. Therefore, the apparatus can operate even when a large vibration occurs in the observation target living body 51 owing to, e.g., some disturbance.

After completing the procedure explained above, the user adjusts the position of the stage 32 such that the marker 53 falls within the range of the above-mentioned ROI. The user then presses "a button for starting a vibration suppressing process" of the user interface 28. Consequently, vibrations of the observation target living body 51 in the X, Y, and Z directions are detected by the processing by the Z-displacement detecting device 20 and Z-displacement detecting circuit 22 and the above-described image processing, and the XYZ stage 6 is driven in a direction to suppress an image blur caused by the vibrations of the observation target living body 51 under the control of the controller 14.

As has been explained above, the biological observation apparatus according to this embodiment can provide a biological observation apparatus and biological observation method using the marker 53 for accurately detecting biological vibrations, and capable of precise biological observation by preventing the marker 53 from being taken in an observation image.

More specifically, since the optical system 38 described above excludes the light from the marker 53, the marker 53 is not taken in the image sensed by the high-sensitivity camera 24, as shown in FIG. 2. This makes it possible to precisely observe the observation target living body 51.

The present invention has been explained above based on the embodiment. However, the present invention is not limited to the above-described embodiment, and various modifications and applications can, of course, be made without departing from the spirit and scope of the invention.

For example, the visual field of the high-speed camera 18 can also be positioned outside the visual field of the high-sensitivity camera 24, so that the marker 53 is not taken in the image sensed by the high-sensitivity camera 24.

It is also possible to integrate the first BA 109 with the high-speed camera 18, and the second BA 107 with the high-sensitivity camera 24.

In addition, the wavelength of the light emitted by the marker 53 may be set in a region where the sensitivity of the high-sensitivity camera 24 is low.

Note that it is, of course, also possible to separate light into its spectral components by using a spectroscope, instead of using the above-described members having the filtering function in the optical system 38, thereby selecting light that enters the high-speed camera 18 and high-sensitivity camera 24 in accordance with the wavelength.

Furthermore, the above-described embodiment includes inventions in various stages, and various inventions can be extracted by appropriately combining the plurality of disclosed constituent elements. For example, even when some of all the constituent elements disclosed in the embodiment are deleted, an arrangement from which these constituent elements are deleted can be extracted as an invention, provided that the problems described in the section of problems to be solved by the invention can be solved, and the effects described in the section of effects of the invention can be obtained.

What is claimed is:

1. A biological observation apparatus for observing a living body, comprising:
    a marker attached to a surface of the living body to detect a vibration of the living body, the marker reflecting or scattering incident light;
    an observation image sensing unit which comprises a first frame rate and forms an observation image of the living body;
    a vibration detecting image sensing unit which comprises a second frame rate higher than the first frame rate and detects light from the marker; and
    an optical system comprising a filtering unit which prevents the light from the marker from entering the observation image sensing unit.

2. The biological observation apparatus according to claim 1, wherein the filtering unit prevents the light from the marker from entering the observation image sensing unit by performing wavelength separation.

3. The biological observation apparatus according to claim 2, wherein excitation light for the fluorescence of the marker is similar to excitation light for a dye having dyed the living body.

4. The biological observation apparatus according to claim 3, wherein a fluorescence intensity of the marker is higher than that of the dye having dyed the living body.

5. The biological observation apparatus according to claim 2, wherein excitation light for the fluorescence of the marker is different from excitation light for a dye having dyed the living body.

6. The biological observation apparatus according to claim 5, wherein a fluorescence intensity of the marker is higher than that of the dye having dyed the living body.

7. The biological observation apparatus according to claim 2, further comprising an illuminating unit which illuminates the marker with white light.

8. The biological observation apparatus according to claim 1, wherein the vibration detecting image sensing unit forms an image of the marker.

* * * * *